(12) United States Patent
Yamamoto et al.

(10) Patent No.: US 11,768,209 B2
(45) Date of Patent: *Sep. 26, 2023

(54) METHOD AND REAGENT FOR MEASURING THYROGLOBULIN

(71) Applicant: FUJIREBIO INC., Tokyo (JP)

(72) Inventors: Kosuke Yamamoto, Hachioji (JP); Yoshiyuki Kitamura, Hachioji (JP); Shintaro Yagi, Hachioji (JP); Katsumi Aoyagi, Hachioji (JP)

(73) Assignee: FUJIREBIO INC., Tokyo (JP)

( * ) Notice: Subject to any disclaimer, the term of this patent is extended or adjusted under 35 U.S.C. 154(b) by 807 days.

This patent is subject to a terminal disclaimer.

(21) Appl. No.: 16/330,549

(22) PCT Filed: Sep. 5, 2017

(86) PCT No.: PCT/JP2017/031869
§ 371 (c)(1),
(2) Date: Mar. 5, 2019

(87) PCT Pub. No.: WO2018/047792
PCT Pub. Date: Mar. 15, 2018

(65) Prior Publication Data
US 2021/0215722 A1 Jul. 15, 2021

(30) Foreign Application Priority Data
Sep. 6, 2016 (JP) .................................. 2016-173835

(51) Int. Cl.
*G01N 33/78* (2006.01)
(52) U.S. Cl.
CPC .................................. *G01N 33/78* (2013.01)
(58) Field of Classification Search
CPC ... G01N 2800/046; G01N 33/78; G01N 33/84
See application file for complete search history.

(56) References Cited

U.S. PATENT DOCUMENTS

| 8,546,075 | B2 * | 10/2013 | Aoyagi | G01N 33/5767 435/5 |
| 2007/0015218 | A1 * | 1/2007 | Cao | G01N 33/537 435/7.2 |
| 2008/0044807 | A1 * | 2/2008 | Aoyagi | G01N 33/5767 435/5 |
| 2009/0042213 | A1 | 2/2009 | Hoofnagle et al. | |
| 2009/0176252 | A1 * | 7/2009 | Kojima | A61P 3/00 435/7.9 |
| 2021/0215680 | A1 * | 7/2021 | Sakaki | G01N 33/53 |

FOREIGN PATENT DOCUMENTS

| EP | 0756173 A1 | 1/1997 |
| EP | 1103814 A1 | 5/2001 |
| JP | 8-220099 A | 8/1996 |
| JP | 2000-241429 A | 9/2000 |
| WO | WO 2014/122973 A1 | 8/2014 |
| WO | WO 2016/005328 A2 | 1/2016 |

OTHER PUBLICATIONS

Communication Pursuant to Rule 164(1) EPC dated Mar. 20, 2020, in European Patent Application No. 17848732.8.
Giovanella et al., "Thyroglobulin measurement using highly sensitive assays in patients with differentiated thyroid cancer: a clinical position paper," European Journal of Endocrinology (2014), vol. 171, pp. R33-R46.
Johnson, M., "Detergents: TritonX-100, Tween-20, and More," Mater Methods (Jan. 21, 2014), XP055131724, Retrieved from the Internet: URL:http://www.laborne.com/method/Detergents-Triton-X-100-Tween-20-and-more.htrnl [retrieved on Jul. 25, 2014].
Kondo, E. and Y. Kondo, "Monoclonal Antibodies to Hog Thyroglobulin Recognizing bisulfide-Dependent Conformational Structures," Molecular Immunology (1984), vol. 21, No. 7, pp. 581-588.
World Health Organization, Use of Anticoagulants in Diagnostic Laboratory Investigations, Jan. 15, 2002, XP055195730, Retrieved from the Internet: URL:http://whqlibdoxwho.int/hq/2002/who_dil_lab_99.1.rev.2.pdf [retrieved on Jun. 15, 2015].
Nishikawa et al., "Thyroglobulin (Tg)," Nihon Rinsho, vol. 68, Special Issue 7, Jul. 20, 2010, pp. 295-298, with partial English translation.
Spencer et al., "Current Status and Performance Goals for Serum Thyroglobulin Assays," Clinical Chemistry, vol. 42, No. 1, 1996, pp. 164-173.
Written Opinion of the International Searching Authority and International Search Report, dated Dec. 12, 2017, for International Application No. PCT/JP2017/031869, with English translations.
Broughton et al., "Characterization of a new highly sensitive immunometric assay for thyroglobulin with reduced interference from autoantibodies," Tumor Biol. (2016), vol. 37, pp. 7729-7739.
Extended European Search Report dated Jun. 9, 2020, in European Patent Application No. 17848732.8.

(Continued)

*Primary Examiner* — Galina M. Yakovleva
(74) *Attorney, Agent, or Firm* — Birch, Stewart, Kolasch & Birch, LLP

(57) ABSTRACT

A measurement method and a measurement reagent for thyroglobulin, which enable measurement of a more accurate amount of thyroglobulin by a single test without being influenced by interference of anti-thyroglobulin antibody, are disclosed. The measurement method for thyroglobulin, wherein thyroglobulin in a sample separated from a body is measured by an immunoassay, includes a pretreatment step of mixing the sample separated from a body with a pretreatment liquid containing one or both of a surfactant and an acidifier. The reagent for immunoassay of thyroglobulin includes a pretreatment liquid containing one or both of a surfactant and an acidifier.

17 Claims, 4 Drawing Sheets

(56) References Cited

OTHER PUBLICATIONS

Hoppe, K. and M. Sznitowska, "The Effect of Polysorbate 20 on Solubility and Stability of Candesartan Cilexetil in Dissolution Media," AAPS PharmSciTech (Oct. 2014), vol. 15, No. 5, pp. 1116-1125.

Rinaldi et al., "Thyroid-Stimulating Hormone, Thyroglobulin, and Thyroid Hormones and Risk of Differentiated Thyroid Carcinoma: The Epic Study," JNCI (Jun. 11, 2014), vol. 106, Issue 6, pp. 1-9.

* cited by examiner

METHOD AND REAGENT FOR MEASURING THYROGLOBULIN

TECHNICAL FIELD

The present invention relates to a measurement method and a measurement reagent for thyroglobulin.

BACKGROUND ART

Thyroglobulin (Tg) is a glycoprotein having a molecular weight of 660,000 produced only in thyroid follicular cells. Biosynthesized Tg is released into the follicular lumen. In this process, binding of iodine molecules to tyrosine groups in the Tg molecule occurs by the action of peroxidase, to cause synthesis of thyroid hormone. Tg in the follicular lumen is incorporated again into the follicular cells, and decomposed in the follicular cells to cause release of the thyroid hormone. This process is activated by the action of thyroid-stimulating hormone (TSH). Thus, under normal conditions, release of Tg itself into blood hardly occurs, and release of Tg into blood indicates a certain abnormality of the thyroid. Therefore, Tg is an extremely useful marker for thyroid diseases because of its high organ specificity. In particular, blood Tg is used as a marker for evaluation of operations for differentiated thyroid cancer, and as a marker for knowing the presence or absence of postoperative recurrence or metastasis. In addition, for example, it is useful as an index of the effect of treatment and remission of Basedow disease, and also useful for identification or differential diagnosis of the disease type, and therapeutic monitoring, of congenital hypothyroidism. It has also been suggested that combination with diagnostic imaging may enable preoperative diagnosis of nodular goiter and differential diagnosis between a benign thyroid disease and a malignant tumor.

However, in cases where the subject is positive for anti-thyroglobulin antibody (TgAb), a low Tg value may be found due to a problem in the measurement even when the actual value of Tg is high. For example, since 20 to 30% of patients with thyroid cancer are positive for TgAb, simultaneous measurement of TgAb has been necessary for measurement of Tg. Further, accurate measurement of the amount of Tg is difficult in cases of Hashimoto disease with TgAb positivity, and, similarly, there has been a possibility that the amount of Tg measured in cases of another autoimmune disease showing TgAb positivity (Basedow disease) has been inaccurate.

PRIOR ART DOCUMENT

Non-Patent Document

[Non-patent Document 1] Spencer C A, Takeuchi M and Kazarosyan M: Current status and performance goals for serum thyroglobulin assays, Clin Chem, 42, 164-173 (1996)

SUMMARY OF THE INVENTION

Problems to be Solved by the Invention

If accurate measurement of the amount of Tg is possible also for the above-described patients with TgAb positivity, its extensive application to therapeutic monitoring of thyroid diseases may be possible. An object of the present invention is to provide a measurement method and a measurement reagent for thyroglobulin which enable measurement of a more accurate amount of thyroglobulin by a single test without being influenced by interference of anti-thyroglobulin antibody.

Means for Solving the Problems

As a result of intensive study to achieve the above object, the present inventors discovered that, in measurement of thyroglobulin in a biological sample, a more accurate measured value of thyroglobulin can be obtained without being influenced by anti-thyroglobulin antibody by carrying out, before subjecting the biological sample to an immune reaction, a pretreatment step of mixing with a pretreatment liquid containing one or both of a surfactant and an acidifier, thereby completing the present invention.

The present invention has the following constitution.

(1) A method of measuring, by immunoassay, thyroglobulin in a sample separated from a body, the method comprising a pretreatment step of mixing the sample separated from a body with a pretreatment liquid containing one or both of a surfactant and an acidifier.

(2) The method according to (1), wherein the pretreatment liquid contains an acidifier, and the acidifier has a final concentration of more than 0.05 N and not more than 0.5 N in the pretreatment step.

(3) The method according to (1), wherein the pretreatment liquid contains a surfactant, and the surfactant is an anionic surfactant.

(4) The method according to (3), wherein the pretreatment step is carried out under heat.

(5) A reagent for immunoassay of thyroglobulin, the reagent comprising a pretreatment liquid containing one or both of a surfactant and an acidifier.

Effect of the Invention

According to the present invention, a measurement method and a measurement reagent for thyroglobulin (Tg) can be provided, which method and reagent allow release of Tg from anti-thyroglobulin antibody (TgAb) to reduce the influence of their interaction, thereby enabling more accurate measurement of the amount of Tg contained in a sample even in cases where the sample is a biological sample containing TgAb.

MODE FOR CARRYING OUT THE INVENTION

Figure 1:
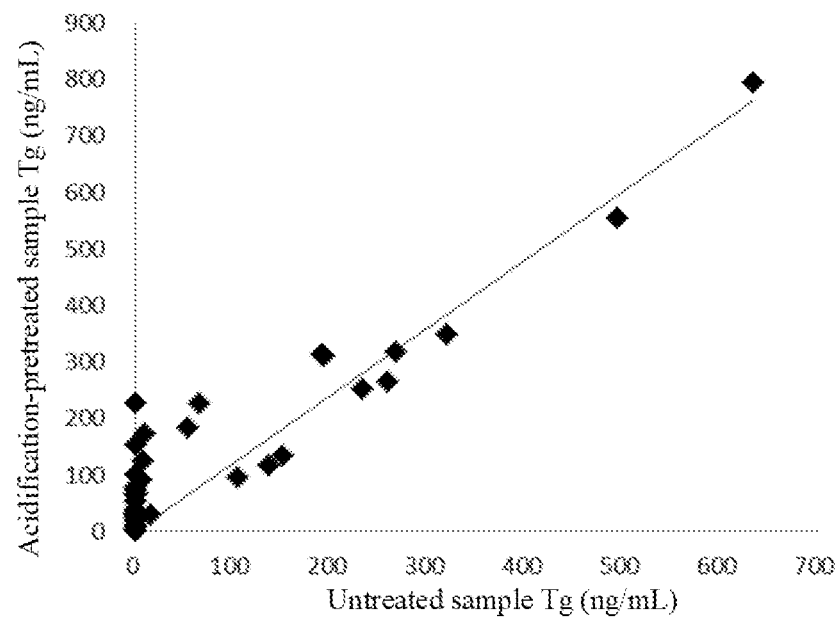
FIG. 1 is a graph for comparison of the measurement results of Tg between the acidification-pretreated samples and the untreated samples.

Unless otherwise specified, the "%" concentration described in the present description is represented as the weight/volume (w/v) concentration.
<Method for Measuring Thyroglobulin>
The thyroglobulin (Tg) to be measured in the present invention is Tg derived from an arbitrary animal. The Tg is preferably Tg derived from a mammal (for example, a primate such as human, monkey, or chimpanzee; a rodent such as mouse, rat, or rabbit; a pet animal such as dog or cat; a domestic animal such as pig or cow; or a working animal such as horse or sheep), more preferably Tg derived from a primate, especially preferably Tg derived from human.
1. Pretreatment Step
The method of the present invention is a method in which Tg present in a biological sample is measured using immune reaction by reacting the biological sample with an antibody. The method is characterized in that it includes a pretreatment step of mixing the biological sample with a pretreatment liquid before the immune reaction (reaction step). By the pretreatment step, Tg can be brought into a state in which it is released from autoantibody (TgAb) or the like. The pretreatment liquid may contain one of a surfactant and an acidifier, or may contain both of these. The pretreatment liquid preferably contains a surfactant or an acidifier.

The volume ratio between the biological sample and the pretreatment liquid to be mixed in the pretreatment step is preferably 1:10 to 10:1, more preferably 1:5 to 5:1, still more preferably 1:3 to 3:1. The biological sample to be used in the present invention is not limited as long as it is a sample that may contain Tg, and examples of the biological sample include serum, plasma, whole blood, urine, stool, oral mucosa, pharyngeal mucosa, intestinal mucosa, and biopsy specimens (for example, thyroid fine needle aspiration cytology (fine needle aspiration: FNA) specimens, intestinal specimens, and liver specimens). The biological sample is preferably serum or plasma.

The surfactant to be contained in the pretreatment liquid may be any of an anionic surfactant, cationic surfactant, zwitterionic surfactant, and nonionic surfactant. The surfactant is especially preferably an anionic surfactant. Preferred examples of the anionic surfactant include sodium dodecyl sulfate (SDS), N-lauroyl sarcosine, lithium dodecyl sulfate, sodium dodecylbenzene sulfonate, and deoxycholic acid. SDS may be especially preferably used. The concentration of the surfactant needs to be sufficient for releasing of Tg from TgAb or the like. In cases where SDS is used, its concentration is preferably 0.1 to 12.5%, more preferably 0.25 to 10%, still more preferably 0.5 to 7.5% in terms of the concentration during the pretreatment of the mixed liquid prepared by mixing with the biological sample. In cases where the SDS concentration is 0.1 to 10%, sufficient release of Tg and suppression of precipitation and the like of SDS can be effectively achieved.

In cases where an anionic surfactant is used as a major surfactant contained in the pretreatment liquid, for reduction of the influence of the anionic surfactant carried over into the reaction system, a neutralization liquid containing one or more of cationic surfactants, zwitterionic surfactants, and nonionic surfactants may be added after the pretreatment.

Preferred examples of the acidifier contained in the pretreatment liquid include hydrochloric acid, sulfuric acid, and acetic acid. In cases where an acidifier is used, the normality of the acid in the pretreatment liquid, in terms of the concentration during the pretreatment, is preferably more than 0.05N and not more than 0.5 N, especially preferably 0.1N to 0.4N. In cases where the normality of the acid is more than 0.05N and not more than 0.5 N, the effect of the pretreatment can be sufficiently obtained, and influence on the subsequent reaction step can be minimized.

In cases where an acidifier is used for the pretreatment, a cationic surfactant is preferably added in order to prevent occurrence of precipitation upon mixing with the biological sample. The cationic surfactant is especially preferably a cationic surfactant having, in a single molecule, a single-chain alkyl group having 10 or more carbon atoms, and a tertiary amine or a quaternary ammonium salt. Examples of such a surfactant include decyltrimethylammonium chloride, dodecyltrimethylammonium chloride, tetradecyltrimethylammonium chloride, hexadecyltrimethyl ammonium chloride (C16TAC), decyltrimethylammonium bromide, dodecyltrimethylammonium bromide, tetradecyltrimethylammonium bromide, hexadecyltrimethylammonium bromide (CTAB), laurylpyridinium chloride, tetradecylpyridinium chloride, and cetylpyridinium chloride. The amount of the cationic surfactant to be added, in temis of the concentration after mixing with the sample, is preferably 0.1% to 15%, more preferably 0.5% to 10%.

The pretreatment liquid containing an acidifier may contain, in addition to the above-mentioned cationic surfactant, another surfactant such as a nonionic surfactant. By the addition of the other surfactant, detection of Tg is possible with an even higher sensitivity.

A reducing agent may also be used for the pretreatment liquid. As the reducing agent, any of known reducing agents such as 2-(diethylamino)ethanethiol hydrochloride (DEAET), tris(2-carboxyethyl)phosphine hydrochloride (TCEP), dithiothreitol (DTT), and 2-mercaptoethanol may be used. From the viewpoint of stability in the solution, DEAET or TCEP may be especially preferably used. The concentration of the reducing agent, in terms of the final concentration in the mixed liquid with the biological sample, is preferably 0.5 to 100 mM, more preferably 1.0 to 50 mM, still more preferably 2.0 to 20 mM.

When necessary, the pretreatment liquid may contain another protein denaturant such as urea or thiourea. The concentration of the denaturant, in terms of the concentration during the treatment, is preferably not less than 0.1 M, more preferably not less than 0.5 M and less than 4 M. For enhancement of the effect of the treatment, the pretreatment liquid may contain any of monosaccharides, disaccharides, citric acid, and citric acid salts, or a combination of these. The pretreatment liquid may also contain a chelating agent such as EDTA.

In the pretreatment step, the mixing of the biological sample with the pretreatment liquid is preferably further followed by heating. In particular, in cases where a surfactant is used for the pretreatment liquid, heating is preferably carried out in order to increase its effect. The heating temperature is preferably 35 to 95° C., more preferably 50 to 90° C., still more preferably 70 to 85° C. The heating time is preferably not less than 1 minute, more preferably not less than 3 minutes, still more preferably not less than 5 minutes. Although there is no upper limit of the heating time, the heating time may be usually not more than 60 minutes, especially not more than 30 minutes.

2. Reaction Step

The biological-sample-mixed liquid obtained by the above-described pretreatment step in the method of the present invention is subsequently subjected to the reaction step of immunoassay. In the reaction step, the biological-sample-mixed liquid is mixed with a buffer, and antigen in the mixed liquid is allowed to react with an antibody against Tg. Regarding the immunoassay itself of Tg, a variety of methods are well known, and any immunoassay capable of quantification of Tg may be employed.

Examples of the buffer include those based on MES buffer, phosphate buffer, Tris buffer, and carbonate buffer. Buffers based on phosphate buffer may be especially preferably used. In cases where a pretreatment liquid containing a surfactant is used, for example, a buffer containing a water-soluble polymer such as BSA, polyvinyl pyrrolidone (PVP), polyvinyl alcohol (PVA), or dextran sulfate sodium at about 0.01 to 10.0%, especially 0.05 to 5.0% in terms of the final concentration after mixing with the pretreated mixed liquid, is preferably used for the purpose of absorbing unreacted surfactant. In cases where a pretreatment liquid containing an acidifier is used, it is preferred to use a buffer containing an alkaline agent or having a buffer capacity capable of decreasing the influence of the acid in the pretreatment liquid. The mixed liquid of the pretreatment step and the buffer are mixed at a volume ratio of preferably 1:10 to 10:1, more preferably 1:5 to 5:1, still more preferably 1:3 to 3:1.

The antibody against Tg to be used in the method of the present invention is an antibody that recognizes at least part of the amino acid sequence of Tg as an epitope. The antibody against Tg is not limited, and any antibody that recognizes a known epitope may be used. The antibody against Tg is preferably an antibody that recognizes a Tg-specific epitope (especially a human Tg-specific epitope).

The antibody against Tg may be either a polyclonal antibody or a monoclonal antibody. The antibody against Tg may be any isotype of immunoglobulins (for example, IgG, IgM, IgA, IgD, IgE, or IgY). The antibody against Tg may be a full-length antibody. The full-length antibody means an antibody containing a heavy chain and a light chain each having a variable region and a constant region (for example, an antibody containing two Fab regions and an Fc region). The antibody against Tg may also be an antibody fragment derived from such a full-length antibody. The antibody fragment is part of a full-length antibody, and examples of the antibody fragment include antibodies lacking the constant region (for example, F(ab')2, Fab', Fab, or Fv). The antibody against Tg may also be a modified antibody such as a single-chain antibody.

The antibody against Tg can be prepared using a conventionally known method. For example, the antibody against Tg can be prepared using the above-described epitope as an antigen. Alternatively, since a number of antibodies against Tg that recognize the above-described epitopes are commercially available, such commercially available products may also be used.

The antibody against Tg may be immobilized on a solid phase. In the present description, an antibody immobilized on a solid phase may be simply referred to as an immobilized antibody. Examples of the solid phase include solid phases in which a liquid phase can be stored or loaded (for example, supports such as plates, membranes, and test tubes; and containers such as well plates, microchannels, glass capillaries, nanopillars, and monolith columns) and solid phases that can be suspended or dispersed in a liquid phase (for example, solid-phase carriers such as particles). Examples of the material of the solid phase include glasses, plastics, metals, and carbons. As the material of the solid phase, a non-magnetic material or a magnetic material may be used. From the viewpoint of simplicity of operation and the like, the material is preferably a magnetic material. The solid phase is preferably a solid-phase carrier, more preferably a magnetic solid-phase carrier, still more preferably a magnetic particle. As the method for immobilization of the antibody, a conventionally known method may be used. Examples of such a method include physical adsorption, covalent bonding, use of an affinity substance (biotin, streptavidin, or the like), and ionic bonding. In a particular embodiment, the antibody against Tg is an antibody immobilized on a solid phase, preferably an antibody immobilized on a magnetic solid phase, more preferably an antibody immobilized on a magnetic particle.

In the reaction step, after the mixing of the mixed liquid of the pretreatment step with the buffer, the resulting mixture may be brought into contact with the immobilized antibody, or, for example, an antibody immobilized on particles may be preliminarily included in a buffer to provide a particle liquid followed by mixing the above mixed liquid with the particle liquid. Although the reaction step may be carried out by a primary reaction step alone as in the immunoagglutination method or the competitive method, a secondary reaction step may also be provided as in the sandwich method. In cases where the secondary reaction step is provided, a washing step for removal of unreacted components may be provided between the primary reaction step and the secondary reaction step.

The antibody against Tg may be labeled with a labeling substance. In the present description, an antibody labeled with a labeling substance may be simply referred to as a labeled antibody. Examples of the labeling substance include enzymes (peroxidase, alkaline phosphatase, luciferase, β-galactosidase, and the like), affinity substances (streptavidin, biotin, and the like), fluorescent substances and proteins (fluorescein, fluorescein isothiocyanate, rhodamine, green fluorescent protein, red fluorescent protein, and the like), luminescent or light-absorbing substances (luciferin, aequorin, acridinium, ruthenium, and the like), and radioactive substances ($^3$H, $^{14}$C, $^{32}$P, $^{35}$S, $^{125}$I, and the like). In cases where the secondary reaction is provided in the method of the present invention, the antibody to be used for the secondary reaction may be labeled with such a labeling substance.

In a particular embodiment, the antibody to be used for the secondary reaction in the method of the present invention includes another antibody against Tg that recognizes an epitope different from that of the above antibody against Tg. Details of such an epitope recognized by the other antibody are the same as the details of the epitope of the above-described antibody against Tg (however, in the case of combined use, the types of the epitopes are different). The combination of the epitope recognized by the antibody against Tg and the epitope recognized by the other antibody against Tg is not limited. Use of such another antibody is preferred in cases where, for example, the sandwich method is used.

3. Detection Step

In cases where a label is used for the primary antibody or the secondary antibody, the detection is carried out by a method suitable for the label used. For example, in cases where an enzyme label is used, the detection is carried out by adding a substrate of the enzyme. For example, in cases where alkaline phosphatase (ALP) is used for the labeled antibody, 3-(2'-spiroadamantane)-4-methoxy-4-(3'-phosphoryloxy)phenyl-1,2-dioxetane disodium salt (AMPPD) may be used as the enzyme substrate to provide a system of the chemiluminescent enzyme immunoassay (CLEIA) method.

The method of the present invention is an immunoassay using an antibody against Tg. Examples of such an immunoassay include the direct competitive method, indirect competitive method, and sandwich method. Further examples of such an immunoassay include chemiluminescent enzyme immunoassay (CLEIA), chemiluminescence immunoassay (CLIA), turbidimetric immunoassay (TIA), enzyme immunoassay (EIA) (for example, direct competitive ELISA, indirect competitive ELISA, and sandwich ELISA), radioimmunoassay (RIA), latex agglutination, fluoroimmunoassay (FIA), and immunochromatography. These immunoassays per se are well known, and do not need to be described herein in detail. A brief description of each immunoassay is given below.

The direct competitive method is a method in which an antibody against a target antigen to be measured (in the present invention, Tg) is immobilized on a solid phase (the solid phase and the immobilization are as described above), and blocking treatment (treatment of the solid phase with a solution of protein such as serum albumin) for prevention of non-specific adsorption is carried out, followed by reacting this antibody with a test sample containing the target antigen (in the present invention, a biological sample subjected to the pretreatment step as described above) and a certain amount of labeled antigen (the label is as described above), performing washing, and then quantifying the label bound to the solid phase. Since the antigen in the test sample and the labeled antigen competitively bind to the antibody, the larger the amount of the antigen in the test sample, the smaller the amount of the label bound to the solid phase. Antigen standard solutions with various known concentrations are prepared, and the amount of the label (the absorbance, luminescence intensity, fluorescence intensity, or the like depending on the properties of the label; the same applies hereinafter) immobilized on the solid phase is measured for each solution, followed by preparation of a calibration curve in which the antigen concentration is taken along the abscissa, and the amount of the label is taken along the ordinate. By measuring the amount of the label for an unknown test sample, and applying the measured amount of the label to the calibration curve, the amount of the antigen in the unknown test sample can be measured. The direct competitive method per se is well known in the art, and described in, for example, US 20150166678 A1.

In the indirect competitive method, a target antigen (in the present invention, Tg) is immobilized on a solid phase (the solid phase and the immobilization are as described above). Subsequently, blocking treatment of the solid phase is carried out, and then a test sample containing the target antigen (in the present invention, a biological sample subjected to the pretreatment step as described above) is mixed with a certain amount of an anti-target-antigen antibody, followed by reaction with the immobilized antigen. After washing, the anti-target-antigen antibody bound to the solid phase is quantified. This can be carried out by allowing reaction with a labeled secondary antibody (the label is as described above) against the anti-target-antigen antibody, performing washing, and then measuring the amount of the label. Antigen standard solutions with various known concentrations are prepared, and the amount of the label immobilized on the solid phase is measured for each solution, followed by preparation of a calibration curve. By measuring the amount of the label for an unknown test sample, and applying the measured amount of the label to the calibration curve, the amount of the antigen in the unknown test sample can be measured. It is also possible to use a labeled primary antibody without using the labeled secondary antibody. The indirect competitive method per se is well known in the art, and described in, for example, the above-mentioned US 20150166678 A1.

The sandwich method is a method in which an anti-target-antigen antibody is immobilized on a solid phase (the solid phase and the immobilization are as described above), and blocking treatment is carried out, followed by reaction with a test sample containing a target antigen (in the present invention, a biological sample subjected to the pretreatment step as described above), washing, reaction with a labeled secondary antibody against the target antigen (the label is as described above), washing, and then quantification of the label bound to the solid phase. Antigen standard solutions with various known concentrations are prepared, and the amount of the label immobilized on the solid phase is measured for each solution, followed by preparation of a calibration curve. By measuring the amount of the label for an unknown test sample, and applying the measured amount of the label to the calibration curve, the amount of the antigen in the unknown test sample can be measured. The sandwich method per se is well known in the art, and described in, for example, US 20150309016 A1.

Among the immunoassays described above, chemiluminescent enzyme immunoassay (CLEIA), chemiluminescence immunoassay (CLIA), enzyme immunoassay (EIA), radioimmunoassay (RIA), and fluoroimmunoassay (FIA) are immunoassays classified based on the type of the label to be used when the direct competitive method, indirect competitive method, sandwich method, or the like described above is carried out. Chemiluminescent enzyme immunoassay (CLEIA) is an immunoassay which uses an enzyme (for example, the above-described alkaline phosphatase) as a label, and uses a substrate that generates a chemiluminescent compound (for example, the above-described AMPPD) as a substrate. Enzyme immunoassay (EIA) is an immunoassay which uses an enzyme (for example, the above-described peroxidase, alkaline phosphatase, luciferase, or β-galactosidase) as a label. As the substrate of each enzyme, a compound quantifiable by measurement of the absorbance or the like is used. For example, in cases of peroxidase, 1,2-phenylenediamine (OPD), 3,3'5,5'-tetramethylbenzidine (TMB), or the like is used. In cases of alkaline phosphatase, p-nitrophenyl phosphate (pNPP) or the like is used. In cases of β-galactosidase, MG: 4-methylumbelliferyl galactoside, NG: nitrophenyl galactoside, or the like is used. In cases of luciferase, luciferin or the like is used. Radioimmunoassay (RIA) is a method which uses a radioactive substance as a label. Examples of the radioactive substance include radioactive elements such as $^3$H, $^{14}$C, $^{32}$P, $^{35}$S, and $^{125}$I as described above. Fluoroimmunoassay (FIA) is a method which uses a fluorescent substance or a fluorescent protein as a label. Examples of the fluorescent substance or the fluorescent protein include, as described above, fluorescein, fluorescein isothiocyanate, rhodamine, green fluorescent protein, and red fluorescent protein. Immunoassays per se using these labels are well known in the art, and described in, for example, U.S. Pat. No. 8,039,223 B and US 20150309016 A1.

Turbidimetric immunoassay (TIA) is an immunoassay which utilizes the phenomenon that an antigen-antibody complex produced by antigen-antibody reaction between a target antigen to be measured (in the present invention, Tg) and an antibody against this antigen causes an increase in the turbidity. The antigen is added, at various known concentrations, to an anti-target-antigen antibody solution, and the turbidity of each resulting mixture is measured to prepare a calibration curve. By similarly measuring the turbidity of an unknown test sample, and applying the measured turbidity to the calibration curve, the amount of the antigen in the unknown test sample can be measured. Turbidimetric immunoassay per se is well known in the art, and described in, for example, US 20140186238 A1. Latex agglutination is a method similar to turbidimetric immunoassay, but uses a suspension of latex particles whose surfaces have an anti-target-antigen antibody immobilized thereon, instead of the antibody solution in turbidimetric immunoassay. Turbidimetric immunoassay and latex agglutination per se are well known in the art, and described in, for example, U.S. Pat. No. 820,398 B.

Immunochromatography is a method in which the above-described sandwich method or competitive method is carried out on a substrate (also called a matrix or a strip) formed with a porous material such as filter paper, cellulose membrane, glass fiber, or non-woven fabric. For example, in cases of immunochromatography by the sandwich method, a detection zone on which an anti-target-antigen antibody is immobilized is provided on the substrate, and a test sample containing a target antigen (in the present invention, a biological sample subjected to the pretreatment step as described above) is added to the substrate, followed by allowing a developer to flow from the upstream side, thereby allowing the target antigen to migrate to the detection zone and immobilizing the target antigen on the detection zone. The immobilized target antigen is sandwiched with a labeled secondary antibody, and the label immobilized on the detection zone is detected to detect the target antigen in the test sample. By forming a labeling zone containing the labeled secondary antibody in the upstream side of the detection zone, the conjugate of the target antigen and the labeled secondary antibody is immobilized on the detection zone. In cases where the label is an enzyme, a substrate zone containing a substrate of the enzyme is also provided in the upstream side of the detection zone. In cases of the competitive method, for example, the target antigen may be immobilized on the detection zone, and the target antigen in the test sample may be allowed to compete with the target antigen immobilized on the detection zone. By providing a labeled antibody zone in the upstream side of the detection zone, allowing the target antigen in the test sample to react with the labeled antibody, immobilizing unreacted labeled antibody on the detection zone, and then detecting or quantifying the label, the target antigen in the test sample can be detected or quantified. Immunochromatography per se is well known in the art, and described in, for example, U.S. Pat. No. 6,210,898 B.

<Measurement Reagent for Tg>

The measurement reagent for Tg of the present invention is a measurement reagent that can realize the above-described measurement method for Tg. The measurement reagent of the present invention is characterized in that it contains, as a constituting component, a pretreatment liquid containing one or both of a surfactant and an acidifier, in addition to the constitution used for ordinary immunoassays.

The reagent of the present invention contains the constituting components in a form in which they are isolated from each other, or in the form of a composition. More specifically, the constituting components may be provided in a form in which they are stored in different containers (for example, tubes or plates), or some of the constituting components may be provided in the form of a composition (for example, in a single solution). Alternatively, the reagent of the present invention may be provided in the form of a device. More specifically, the reagent may be provided in a form in which all constituting components are stored in a device. Alternatively, the reagent may be provided in a form in which some of the constituting components are stored in a device while the remaining constituting components are not stored in the device (for example, in a form in which they are stored in a different container(s)). In such a case, the constituting components not stored in the device may be used by injection into the device when conducting the measurement of the target substance.

In a preferred embodiment, the reagent of the present invention may have a constitution suitable for the type of the immunoassay to be employed. For example, in cases where the sandwich method is employed, the reagent of the present invention may contain, as indispensable constituting components, i) a pretreatment liquid, ii) an antibody against Tg, and iii) a buffer; and, as arbitrary constituting components, iv) another antibody against Tg, v) a labeling substance, vi) a diluent, and, when necessary, vii) a substrate that reacts with the labeling substance. The constituting components ii) and iii) may be contained in a single solution. The constituting component iv) may be labeled with the labeling substance v). The antibody against Tg may be preferably immobilized on magnetic particles.

EXAMPLES

Example 1 Confirmation of Effect of Acidification Pretreatment (ELISA Method)

(1) Preparation of Anti-Thyroglobulin Antibody Plate

To a polystyrene 96-well microwell plate (manufactured by Nunc), an antibody dilution solution (0.1 M sodium hydrogen carbonate, 0.1 M sodium chloride; pH 9.6) containing 5 μg/mL anti-Tg mouse antibody 5F9 (manufactured by AbD Serotec) was dispensed at 100 μL/well, and the plate was then incubated at 4° C. overnight. The microwell plate was washed with PBS three times, and then a blocking liquid (PBS containing 1.0% BSA, 3% sucrose, and 0.05% ProClin (registered trademark) 300) was dispensed at 200 μL/well, followed by incubation at room temperature for 2 hours. After removing the blocking liquid, the plate was dried under vacuum to provide an anti-Tg antibody plate.

(2) Sample Pretreatment

With 50 μL of an acidification pretreatment liquid (2.5 M urea, 0.42 M hydrochloric acid, 0.08 M citric acid hydrate, 2.5% maltose, 10.0% CTAB, 4.9% Triton X-100 (trade name)), 50 μL of each of 45 serum samples from patients with thyroid-related diseases was mixed, and the resulting mixture was warmed at 37° C. for 6 minutes. Subsequently, 100 μL of a buffer (500 mM Tris-HCl, 200 mM NaCl, EDTA 3Na, 10.0% BSA, 50 μg/mL mouse IgG; pH 9.2) was added thereto to provide an acidification-pretreated sample.

In addition, 50 μL of each of the same samples was mixed with 150 μL of a mixture prepared by mixing 50 μL of the acidification pretreatment liquid and 100 μL of the buffer (neutralization liquid), to provide an untreated sample.

Purified human Tg (manufactured by BBI solutions) with a known concentration was diluted with TgAb-negative serum, to provide 0, 10, 50, 200, and 400 ng/mL standard solutions. Also for each standard solution, an acidification-pretreated sample and an untreated sample were prepared by the same method as described above.

(3) Measurement of Tg in Samples

To an anti-Tg antibody plate, 150 µL of each of the acidification-pretreated samples and the untreated samples was dispensed, and the plate was then incubated at room temperature for 1 hour (primary reactions). After five times of washing with a washing liquid (0.05% Tween 20/PBS), a secondary antibody liquid prepared by diluting a biotinylated anti-Tg antibody 5E6 (manufactured by AbD Serotec) to 2 µg/mL in a secondary reaction liquid (24 mM potassium dihydrogen phosphate, 76 mM dipotassium hydrogen phosphate, 1.0% BSA, 1.0% PVP, 0.05% casein sodium, 0.05% Tween 20, 0.05% sodium chloride, 20 mM EDTA 2Na, 0.1% ProClin 300 (registered trademark); pH 7.0) was dispensed at 100 µL/well, and the reaction was allowed to proceed at room temperature for 1 hour (secondary reaction). After five times of washing with the washing liquid, an HRP-labeled streptavidin (manufactured by Roche) liquid diluted 10,000-fold with the secondary reaction liquid was dispensed at 100 µL/well, and the reaction was allowed to proceed at room temperature for 30 minutes. After five times of washing with the washing liquid, TMB substrate liquid (manufactured by Nacalai Tesque, Inc.) was dispensed at 100 µL/well, and the plate was left to stand at room temperature for 15 minutes in the dark. By dispensing 1N sulfuric acid at 100 µL/well, the reaction was stopped, and the absorbance at 450 nm/630 nm was measured for each well. The measured value of Tg for each sample was calculated based on a calibration curve prepared using the acidification-pretreated standard solutions and the untreated standard solutions. All samples showing an absorbance lower than that of the 0 ng/mL standard solution were regarded as having a measured value of 0 ng/mL.

Separately, "Lumipulse (registered trademark) TgAb" (manufactured by Fujirebio Inc.) was used for measuring the TgAb value for each sample.

(4) Results

Figure 2:
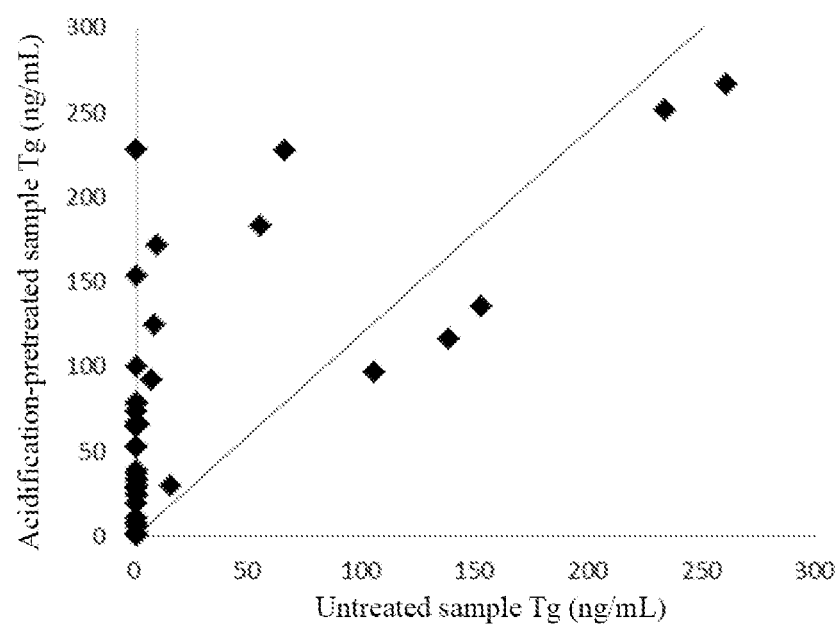
FIG. 2 is a graph for comparison of the measurement results of Tg between the acidification-pretreated samples and the untreated samples.

Table 1 shows the measurement results for the acidification-pretreated sample and the untreated sample for each of the samples and the standard solutions. FIG. 1 shows correlation of all measured values for the acidification-pretreated samples and the untreated samples, and FIG. 2 specifically shows correlation in a low-absorbance region. Untreated samples with especially high TgAb values tended to show absorbances lower than 0 ng/mL, but the absorbances increased by the pretreatment. It was thus suggested that the measurement became possible also for samples for which measurement of Tg has so far been impossible.

TABLE 1

|  |  | TgAb | Absorbance | | Measured value (ng/ml) | | Treated/ |
|---|---|---|---|---|---|---|---|
|  |  | (IU/mL) | Untreated | Treated | Untreated | Treated | Untreated |
| Sample | 1 | 14.8 | 1.4779 | 1.1566 | 267.7 | 318.0 | 1.19 |
| No. | 2 | 11.1 | 0.9113 | 0.5524 | 152.0 | 134.9 | 0.89 |
|  | 3 | 12.0 | 0.6820 | 0.4254 | 105.2 | 96.4 | 0.92 |
|  | 4 | 12.4 | 1.3089 | 0.9375 | 233.2 | 251.6 | 1.08 |
|  | 6 | 1213.1 | 0.1030 | 0.8597 | 0 | 228.0 | — |
|  | 7 | 86.7 | 1.7345 | 1.2558 | 320.0 | 348.0 | 1.09 |
|  | 8 | 213.4 | 0.2431 | 0.2044 | 15.7 | 29.4 | 1.88 |
|  | 9 | 262.8 | 0.2006 | 0.4107 | 7.0 | 91.9 | 13.13 |
|  | 10 | 1651.4 | 0.0554 | 0.2281 | 0 | 36.6 | — |
|  | 11 | 20.4 | 3.2788 | 2.7310 | 635.2 | 795.1 | 1.25 |
|  | 12 | 23.9 | 2.5948 | 1.9382 | 495.6 | 554.8 | 1.12 |
|  | 13 | 120.7 | 1.4408 | 0.9863 | 260.1 | 266.4 | 1.02 |
|  | 14 | 89.1 | 1.1165 | 1.1293 | 193.9 | 309.7 | 1.60 |
|  | 16 | 165.6 | 0.0771 | 0.1996 | 0 | 28.0 | — |
|  | 17 | 325.1 | 0.0990 | 0.2829 | 0 | 53.2 | — |
|  | 18 | 9853.5 | 0.0220 | 0.1438 | 0 | 11.1 | — |
|  | 19 | 713.2 | 0.0706 | 0.2803 | 0 | 52.4 | — |
|  | 20 | 602.1 | 0.1115 | 0.3229 | 0 | 65.3 | — |
|  | 21 | 1770.8 | 0.0207 | 0.0867 | 0 | 0 | — |
|  | 22 | 1514.5 | 0.0173 | 0.1127 | 0 | 1.6 | — |
|  | 23 | 518.0 | 0.0521 | 0.1882 | 0 | 24.5 | — |
|  | 24 | 3510.8 | 0.0493 | 0.2161 | 0 | 33.0 | — |
|  | 25 | 336.8 | 0.0539 | 0.1253 | 0 | 5.5 | — |
|  | 26 | 392.6 | 0.0649 | 0.2165 | 0 | 33.1 | — |
|  | 27 | 871.8 | 0.4888 | 0.8581 | 65.8 | 227.5 | 3.46 |
|  | 28 | 318.6 | 0.8411 | 0.4918 | 137.7 | 116.5 | 0.85 |
|  | 29 | 400.8 | 0.0541 | 0.1333 | 0 | 7.9 | — |
|  | 30 | 8675.7 | 0.0371 | 0.2004 | 0 | 28.2 | — |
|  | 31 | 854.7 | 0.0613 | 0.2357 | 0 | 38.9 | — |
|  | 32 | 325.2 | 0.0345 | 0.1705 | 0 | 19.2 | — |
|  | 33 | 84.3 | 0.0837 | 0.1841 | 0 | 23.3 | — |
|  | 34 | 230.9 | 0.0587 | 0.3643 | 0 | 77.9 | — |
|  | 35 | 265.0 | 0.1731 | 0.3243 | 1.4 | 65.8 | 47.38 |
|  | 36 | 182.8 | 0.0989 | 0.2046 | 0 | 29.5 | — |
|  | 37 | 597.6 | 0.0959 | 0.3199 | 0 | 64.4 | — |
|  | 38 | 513.3 | 0.1239 | 0.4359 | 0 | 99.6 | — |
|  | 39 | 502.9 | 0.1642 | 0.3493 | 0 | 73.3 | — |
|  | 40 | 442.5 | 0.0542 | 0.6125 | 0 | 153.1 | — |
|  | 41 | 162.1 | 1.1045 | 1.1371 | 191.5 | 312.1 | 1.63 |
|  | 42 | 389.0 | 0.2067 | 0.5186 | 8.2 | 124.6 | 15.12 |
|  | 43 | 456.9 | 0.1563 | 0.3656 | 0 | 78.3 | — |
|  | 44 | 3854.7 | 0.1133 | 0.3264 | 0 | 66.4 | — |

TABLE 1-continued

|  | TgAb (IU/mL) | Absorbance Untreated | Absorbance Treated | Measured value (ng/ml) Untreated | Measured value (ng/ml) Treated | Treated/ Untreated |
|---|---|---|---|---|---|---|
|  | 45 | 488.9 | 0.2112 | 0.6735 | 9.2 | 171.6 | 18.72 |
|  | 46 | 198.1 | 0.4351 | 0.7113 | 54.9 | 183.0 | 3.34 |
|  | 47 | 249.6 | 0.0858 | 0.0561 | 0 | 0 | — |
| Standard solution (ng/mL) | 0 | — | 0.1060 | 0.0670 | — | — | — |
|  | 10 | — | 0.2060 | 0.1230 | — | — | — |
|  | 50 | — | 0.4530 | 0.2940 | — | — | — |
|  | 200 | — | 1.2220 | 0.8590 | — | — | — |
|  | 400 | — | 2.1000 | 1.4030 | — | — | — |

Example 2 Gel Filtration Test of Acidification-Pretreated Samples

Untreated samples and acidification-pretreated samples were prepared for sample No. 6, whose measured value increased by the pretreatment, and sample No. 13, whose measured value did not change by the pretreatment, in Example 1. The prepared samples were subjected to gel filtration chromatography.

Each untreated sample was prepared by mixing 100 μL of each sample with 300 μL of the neutralization liquid. Each acidification-pretreated sample was prepared by mixing 100 μL of each sample with 100 μL of the acidification pretreatment liquid, and then warming the resulting mixture at 37° C. for 6 minutes, followed by adding 200 μL of the buffer thereto. Each prepared sample was filtered through a 0.45-μm filter, and then 250 μL of the resulting filtrate was applied to a gel filtration column.

Separation Conditions
  Column: Superose 6 10/30 (trade name)
  Separation buffer: PBS, 0.08% CHAPS, 0.05% Tween 20 (trade name), 1 mM EDTA 2Na; pH 7.4
  Flow rate: 0.5 mL/minute
  Collection range: 4 mL to 24 mL (0.5 mL/fraction)

Each collected fraction was subjected to Tg measurement by the same ELISA method as in Example 1 without carrying out further pretreatment.

In addition, protein molecular weight markers (manufactured by GE, containing thyroglobulin) were subjected to gel filtration under the same conditions, and the UV absorbance was measured.

Figure 3:
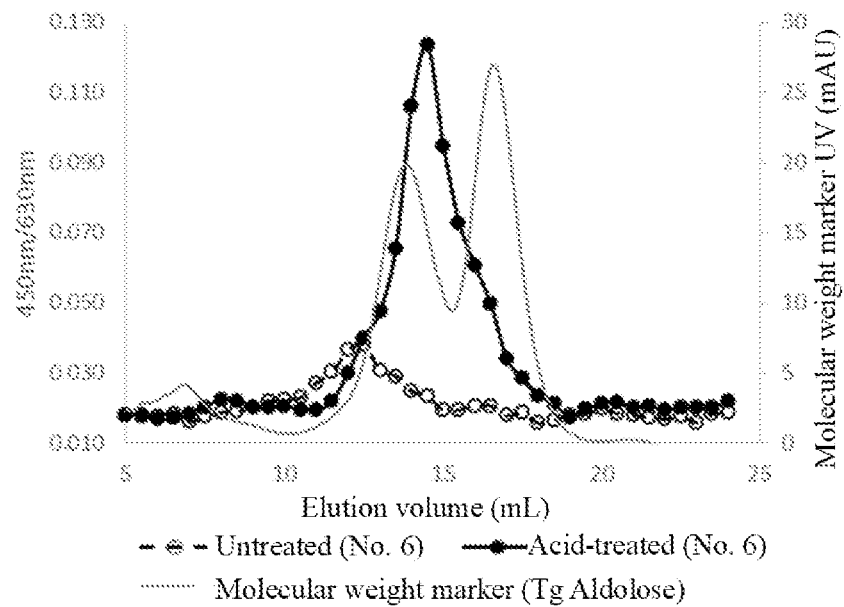
FIG. 3 is the result of chromatography of a serum sample showing deviation of the Tg measurement result between the acidification-pretreated sample and the untreated sample, wherein the acidified sample and the untreated sample were subjected to a gel filtration column.
Figure 4:
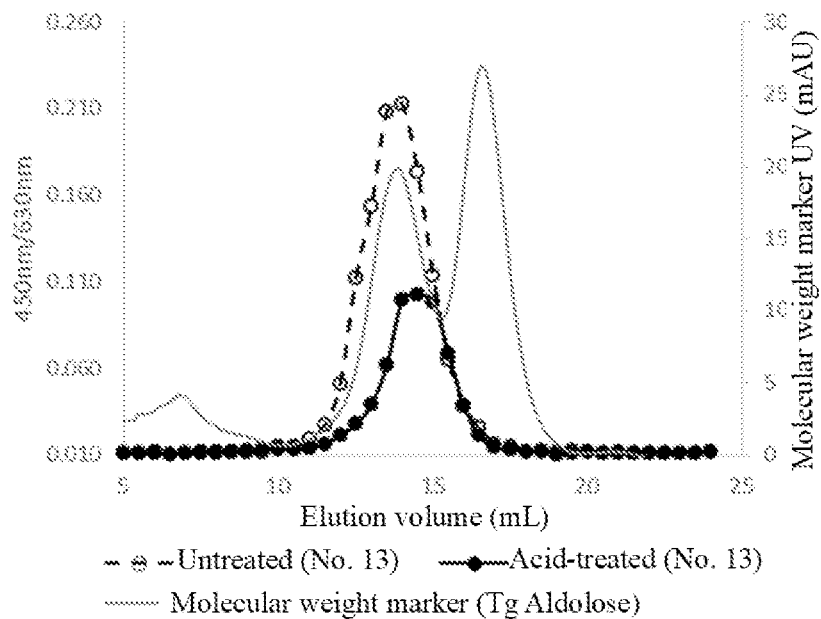
FIG. 4 is the result of chromatography of a serum sample showing no difference in the Tg measurement result between the acidification-pretreated sample and the untreated sample, wherein the acidified sample and the untreated sample were subjected to a gel filtration column.

The measurement results for the fractions of sample No. 6 are shown in FIG. 3, and the measurement results for the fractions of sample No. 13 are shown in FIG. 4. Regarding sample No. 6, while the untreated sample showed a small peak of the measured Tg value in a region with a molecular weight higher than that of Tg, the acidification-pretreated sample showed a peak of the measured Tg value in a region with the same molecular weight as that of Tg. Regarding sample No. 13, both the untreated sample and the acidification-pretreated sample showed a peak of the measured Tg value in a region with the same molecular weight as that of Tg. It is thought that the acidification-pretreated sample showed a decreased signal due to the influence of the acid. From these results, it was suggested that, while the untreated sample of sample No. 6, whose measured values increased by the pretreatment, had decreased reactivity in the Tg measurement system due to increases in the molecular weight by formation of complexes of thyroglobulin and TgAb or the like, the acidification pretreatment caused release of Tg from the complexes, leading to increased reactivity in the Tg measurement system.

Example 3 Optimum Concentration of Acidifier

The optimum concentration of the acidifier to be used for the acidification pretreatment was studied. Fifty microliters of each of a total of six samples, more specifically, samples No. 13 and No. 16, which were positive for TgAb and showed relatively weak influence (interference) of TgAb on the measured Tg values, samples No. 19 and No. 44, which were positive for TgAb and showed relatively strong interference of TgAb, and samples No. 25 and No. 30, which were negative for TgAb, was mixed with 50 μL of an acidification pretreatment liquid prepared in the same manner as the acidification pretreatment liquid in Example 1 except that it contained 2 N, 1 N, 0.8 N, 0.6 N, 0.4 N, 0.2 N, 0.1 N, 0.05 N, 0.025 N, or 0 N hydrochloric acid, and the resulting mixture was warmed at 37° C. for 6 minutes. Subsequently, 100 μL of sodium hydroxide solution equivalent to the hydrochloric acid was added thereto for neutralization. To the neutralized solution, 200 μL of the same secondary reaction liquid as in Example 1 was added to provide an acidification-pretreated sample. Each acidification-pretreated sample was subjected to the same ELISA method as in Example 1 to obtain absorbance data at 450 nm/630 nm.

Figure 5:
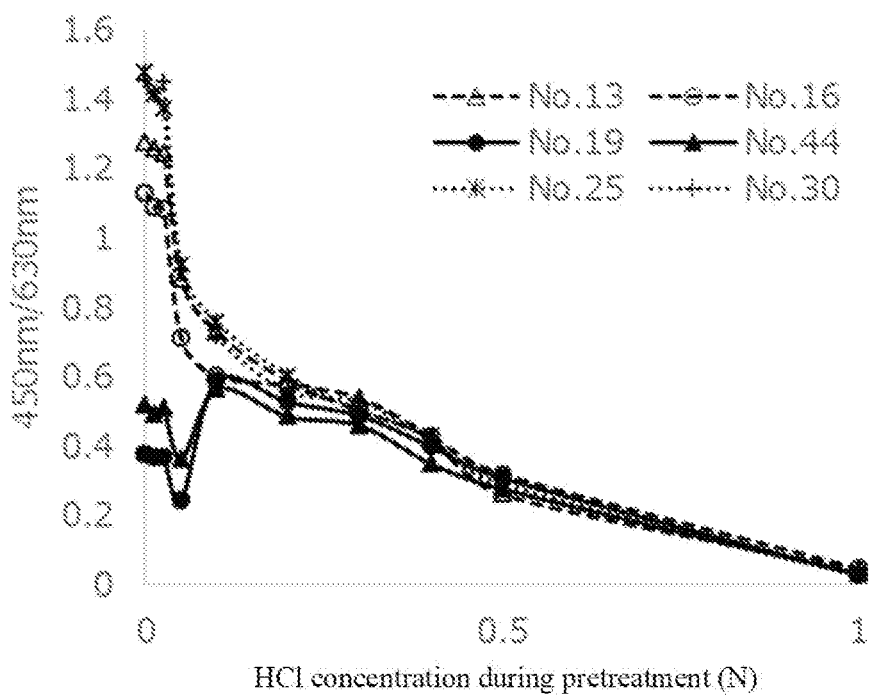
FIG. 5 is a graph showing correlation between the acid concentration in the acidification pretreatment liquid and the measured Tg value of each sample.

The absorbance data for each sample are shown in Table 2 and FIG. 5. In the samples negative for TgAb and the samples showing weak competition with TgAb, the absorbances tended to decrease as the acidifier concentration in the pretreatment liquid increased. This is thought to be because denaturation of Tg occurred due to the influence by the acid, and because the antigen-antibody reaction was inhibited due to the influence by the salt produced during the neutralization. However, in the two samples showing strong competition with TgAb, although the absorbances in the region with high acidifier concentrations were low, the absorbances at an acidifier concentration of 0.1 N were higher than those in the state where the acidifier was absent. Under the conditions where the acidifier concentration exceeded 0.05 N, these samples showed absorbances equivalent to those of other samples in which the influence of TgAb was low, and, as the acidification concentration increased, the absorbances decreased similarly to other samples. On the other hand, in the cases where the acidifier concentration exceeded 0.5 N, the absorbances decreased almost to the blank, and therefore Tg measurement was difficult as a whole.

Thus, it was found that, in order to enable measurement of samples with strong interference by TgAb similarly to other samples, the concentration of the acidifier in the acidification pretreatment liquid during the pretreatment is preferably more than 0.05 N and not more than 0.5 N, especially preferably 0.1 N to 0.4 N.

TABLE 2

| HCl concentration (N) | TgAb (+) | | | | TgAb (−) | |
|---|---|---|---|---|---|---|
| | During Pretreatment | | | | | |
| | Autoantibody (+), weak interference | | Autoantibody (+), strong interference | | No autoantibody | |
| | No. 13 | No. 16 | No. 19 | No. 44 | No. 25 | No. 30 |
| 1 | 0.042 | 0.047 | 0.028 | 0.031 | 0.027 | 0.030 |
| 0.5 | 0.261 | 0.319 | 0.308 | 0.276 | 0.280 | 0.292 |
| 0.4 | 0.425 | 0.426 | 0.399 | 0.349 | 0.426 | 0.417 |
| 0.3 | 0.539 | 0.503 | 0.488 | 0.460 | 0.505 | 0.530 |
| 0.2 | 0.589 | 0.573 | 0.527 | 0.485 | 0.603 | 0.557 |
| 0.1 | 0.729 | 0.602 | 0.588 | 0.565 | 0.757 | 0.715 |
| 0.05 | 0.883 | 0.711 | 0.245 | 0.364 | 0.923 | 0.907 |
| 0.025 | 1.242 | 1.083 | 0.368 | 0.508 | 1.371 | 1.450 |
| 0.0125 | 1.256 | 1.089 | 0.366 | 0.492 | 1.412 | 1.418 |
| 0 | 1.274 | 1.131 | 0.377 | 0.519 | 1.478 | 1.455 |

Example 4 Test for Confirmation of Effect of SDS Pretreatment (ELISA Method)

Fifty microliters of each of 51 serum samples from patients with thyroid-related diseases was mixed with 100 μL of an SDS pretreatment liquid (347 mM SDS, 2 mM EDTA 2Na, 10 mM Tris-HCl; pH7.2), and the resulting mixture was heated at 80° C. for 5 minutes with shaking at 1000 rpm. Subsequently, the mixture was diluted 4-fold with a neutralization liquid (1.2% C16TAC, 4% CHAPS, 2.9% Tween 20 (trade name)), and the resulting dilution solution was incubated at room temperature for 30 minutes, followed by performing centrifugation at 15° C. at 12,000 rpm for 15 minutes to obtain a supernatant as an SDS-pretreated sample. In addition, the same samples were treated in the same manner as in the above SDS pretreatment except that 100 μL of PBS was used instead of the pretreatment liquid and that heating was not carried out, to obtain untreated samples. Purified human Tg (manufactured by BBI solutions) with a known concentration was diluted with TgAb-negative serum, to prepare 0, 6, 30, 60, 300, 600, 2400, and 4800 ng/mL standard solutions. Also for each standard solution, an SDS-pretreated sample and an untreated sample were prepared by the same method as described above.

After mixing 100 μL of each of the SDS-pretreated sample and the untreated sample with 100 μL of a buffer (50 mM Tris, 150 mM NaCl, 1 mM EDTA 2Na, 6.0% BSA, 0.05% ProClin 300 (registered trademark); pH 7.2), 150 μL of the resulting mixture was dispensed to an anti-Tg antibody plate prepared by the same method as in Example 1. The plate was then incubated at room temperature for 2 hours. After five times of washing with a washing liquid (0.05% Tween 20 (trade name)/PBS), a secondary antibody liquid prepared by diluting a biotinylated anti-Tg antibody 5E6 (manufactured by AbD Serotec) to 2 μg/mL in a secondary reaction liquid (24 mM potassium dihydrogen phosphate, 76 mM dipotassium hydrogen phosphate, 1.0% BSA, 1.0% PVP, 0.05% casein sodium, 0.05% Tween 20 (trade name), 0.05% sodium chloride, 20 mM EDTA 2Na, 0.1% ProClin 300 (registered trademark); pH 7.0) was dispensed at 100 μL/well, and the reaction was allowed to proceed at room temperature for 1 hour (secondary reaction). After five times of washing with the washing liquid, an HRP-labeled streptavidin (manufactured by Roche) liquid diluted 10,000-fold with the secondary reaction liquid was dispensed at 100 μL/well, and the reaction was allowed to proceed at room temperature for 30 minutes. After five times of washing with the washing liquid, TMB substrate liquid (manufactured by Nacalai Tesque, Inc.) was dispensed at 100 μL/well, and the plate was left to stand at room temperature for 15 minutes in the dark. By dispensing 1N sulfuric acid at 100 μL/well, the reaction was stopped, and the absorbance at 450 nm/630 nm was measured for each well. The measured value of Tg for each sample was calculated based on a calibration curve prepared using the SDS-pretreated standard solutions and the untreated standard solutions. All samples showing an absorbance lower than that of the 0 ng/mL standard solution were regarded as having a measured value of 0 ng/mL.

Separately, Lumipulse (registered trademark) TgAb (manufactured by Fujirebio Inc.) was used for measuring the TgAb value for each sample.

Figure 6:
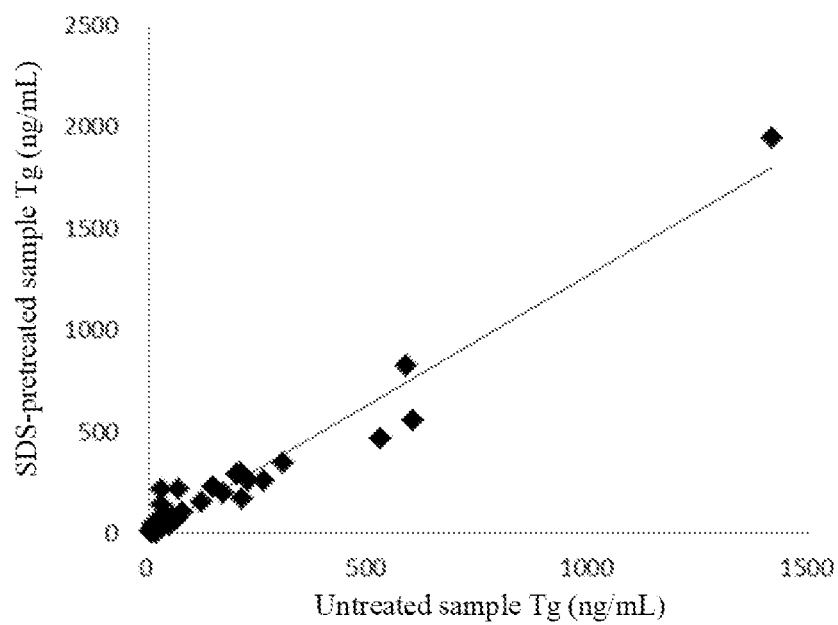
FIG. 6 is a graph for comparison of the Tg measurement results between the SDS-pretreated samples and the untreated samples.
Figure 7:
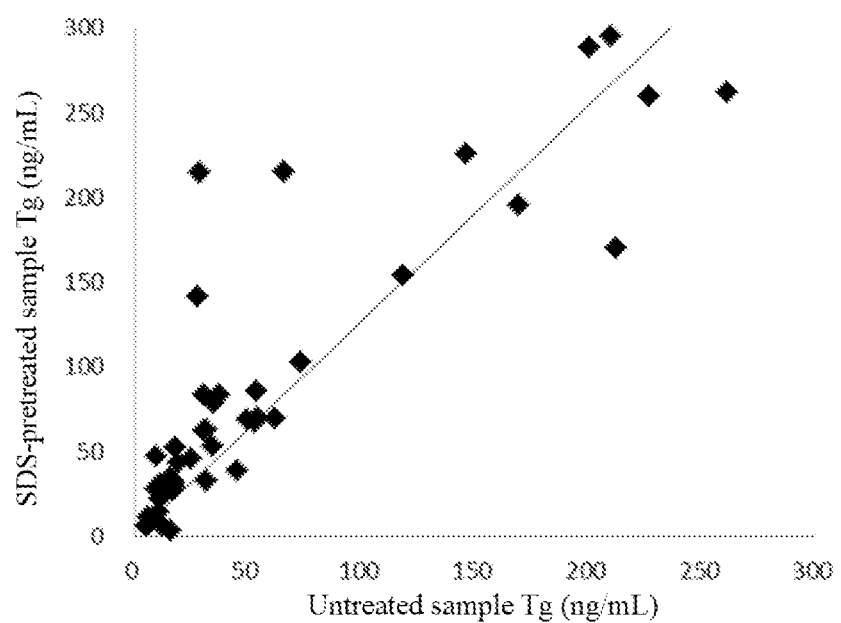
FIG. 7 is a graph for comparison of the Tg measurement results between the SDS-pretreated samples and the untreated samples.

Table 3 shows the measurement results for the SDS-pretreated sample and the untreated sample for each of the samples and the standard solutions. FIG. 6 shows correlation of all measured values for the acidification-pretreated samples and the untreated samples, and FIG. 7 specifically shows correlation in a low-absorbance region. Untreated samples with especially high TgAb values tended to show absorbances near 0 ng/mL, but the absorbances increased by the pretreatment, which suggests that the falsely low values were improved.

TABLE 3

| | | TgAb | Absorbance | | Measured value | | Treated/ |
|---|---|---|---|---|---|---|---|
| | | (IU/mL) | Untreated | Pretreated | Untreated | Pretreated | Untreated |
| Sample No. | 51 | | 0.2890 | 0.1881 | 200.4 | 288.3 | 1.44 |
| | 52 | 11.1 | 0.1743 | 0.1076 | 118.5 | 154.2 | 1.30 |
| | 53 | 12.0 | 0.1117 | 0.0766 | 73.8 | 102.5 | 1.39 |
| | 54 | 12.4 | 0.3025 | 0.1923 | 210.1 | 295.3 | 1.41 |
| | 55 | 14.9 | 0.0959 | 0.0569 | 62.5 | 69.7 | 1.11 |
| | 56 | 1213.1 | 0.0493 | 0.1440 | 29.2 | 214.8 | 7.35 |
| | 57 | 86.7 | 0.7445 | 0.2949 | 525.8 | 466.3 | 0.89 |
| | 58 | 213.4 | 0.0720 | 0.0383 | 45.4 | 38.7 | 0.85 |
| | 59 | 262.8 | 0.0526 | 0.0529 | 31.6 | 63.0 | 2.00 |
| | 60 | 1651.4 | 0.0247 | 0.0331 | 11.6 | 30.0 | 2.58 |
| | 61 | 20.4 | 1.9906 | 1.1809 | 1415.9 | 1943.0 | 1.37 |
| | 62 | 23.9 | 0.8271 | 0.5108 | 584.8 | 826.2 | 1.41 |
| | 63 | 120.7 | 0.3743 | 0.1723 | 261.4 | 262.0 | 1.00 |
| | 64 | 89.1 | 0.4362 | 0.2232 | 305.6 | 346.8 | 1.14 |
| | 65 | 49.3 | 0.8454 | 0.3472 | 597.9 | 553.5 | 0.93 |

TABLE 3-continued

|  | TgAb (IU/mL) | Absorbance | | Measured value | | Treated/ |
|---|---|---|---|---|---|---|
|  |  | Untreated | Pretreated | Untreated | Pretreated | Untreated |
|  | 66 | 165.6 | 0.0322 | 0.0348 | 17.0 | 32.8 | 1.93 |
|  | 67 | 325.1 | 0.0358 | 0.0412 | 19.6 | 43.5 | 2.22 |
|  | 68 | 9853.5 | 0.0156 | 0.0190 | 5.1 | 6.5 | 1.26 |
|  | 69 | 713.2 | 0.0339 | 0.0465 | 18.2 | 52.3 | 2.87 |
|  | 70 | 602.1 | 0.0784 | 0.0562 | 50.0 | 68.5 | 1.37 |
|  | 71 | 1770.8 | 0.0174 | 0.0192 | 6.4 | 6.8 | 1.06 |
|  | 72 | 1514.5 | 0.0177 | 0.0191 | 6.6 | 6.7 | 1.00 |
|  | 73 | 518.0 | 0.0307 | 0.0355 | 15.9 | 34.0 | 2.13 |
|  | 74 | 3510.8 | 0.0301 | 0.0350 | 15.5 | 33.2 | 2.14 |
|  | 75 | 336.8 | 0.0239 | 0.0239 | 11.1 | 14.7 | 1.32 |
|  | 76 | 392.6 | 0.0242 | 0.0285 | 11.3 | 22.3 | 1.98 |
|  | 77 | 871.8 | 0.2129 | 0.1504 | 146.1 | 225.5 | 1.54 |
|  | 78 | 318.6 | 0.3055 | 0.1171 | 212.2 | 170.0 | 0.80 |
|  | 79 | 400.8 | 0.0334 | 0.0330 | 17.9 | 29.8 | 1.67 |
|  | 80 | 8675.7 | 0.0301 | 0.0321 | 15.5 | 28.3 | 1.83 |
|  | 81 | 854.7 | 0.0435 | 0.0423 | 25.1 | 45.3 | 1.81 |
|  | 82 | 325.2 | 0.0224 | 0.0321 | 10.0 | 28.3 | 2.83 |
|  | 83 | 84.3 | 0.0327 | 0.0313 | 17.4 | 27.0 | 1.56 |
|  | 84 | 230.9 | 0.0224 | 0.0433 | 10.0 | 47.0 | 4.70 |
|  | 85 | 265.0 | 0.0832 | 0.0556 | 53.4 | 67.5 | 1.26 |
|  | 86 | 182.8 | 0.0568 | 0.0468 | 34.6 | 52.8 | 1.53 |
|  | 87 | 597.6 | 0.0511 | 0.0648 | 30.5 | 82.8 | 2.72 |
|  | 88 | 513.3 | 0.0575 | 0.0622 | 35.1 | 78.5 | 2.24 |
|  | 89 | 502.9 | 0.0845 | 0.0569 | 54.4 | 69.7 | 1.28 |
|  | 90 | 442.5 | 0.0477 | 0.1000 | 28.1 | 141.5 | 5.04 |
|  | 91 | 162.1 | 0.3261 | 0.1711 | 226.9 | 260.0 | 1.15 |
|  | 92 | 389.0 | 0.0611 | 0.0649 | 37.6 | 83.0 | 2.20 |
|  | 93 | 456.9 | 0.0838 | 0.0662 | 53.9 | 85.2 | 1.58 |
|  | 94 | 3854.7 | 0.0527 | 0.0347 | 31.6 | 32.7 | 1.03 |
|  | 95 | 488.9 | 0.1014 | 0.1443 | 66.4 | 215.3 | 3.24 |
|  | 96 | 198.1 | 0.2452 | 0.1325 | 169.1 | 195.7 | 1.16 |
|  | 97 | 249.6 | 0.0257 | 0.0187 | 12.4 | 6.0 | 0.49 |
|  | 98 | 301.8 | 0.0321 | 0.0339 | 16.9 | 31.3 | 1.85 |
|  | 99 | 1228.9 | 0.0172 | 0.0218 | 6.3 | 11.2 | 1.78 |
|  | 100 | 356.9 | 0.0311 | 0.0172 | 16.2 | 3.5 | 0.22 |
|  | 101 | 229.0 | 0.0513 | 0.0524 | 30.6 | 62.2 | 2.03 |
| Standard solution (ng/mL) | 0 | — | 0.0225 | 0.0176 | — | — | — |
|  | 6 | — | 0.0285 | 0.0242 | — | — | — |
|  | 30 | — | 0.0651 | 0.0362 | — | — | — |
|  | 60 | — | 0.0915 | 0.0546 | — | — | — |
|  | 300 | — | 0.3824 | 0.2001 | — | — | — |
|  | 600 | — | 0.8843 | 0.4082 | — | — | — |
|  | 2400 | — | 2.2429 | 1.2609 | — | — | — |
|  | 4800 | — | 2.8909 | 1.9778 | — | — | — |

The invention claimed is:

1. A method of measuring, by immunoassay, thyroglobulin in a sample separated from a body, the method comprising (a) a pretreatment step of mixing the sample separated from a body with a pretreatment liquid to produce a pretreated sample, said pretreatment liquid containing an acidifier or an anionic surfactant, wherein when the pretreatment liquid contains an acidifier, the pretreatment liquid further contains a cationic surfactant, and (b) subsequently mixing said pretreated sample with a buffer containing a water-soluble polymer.

2. The method according to claim 1, wherein the pretreatment liquid contains an acidifier, and the acidifier has a final concentration of more than 0.05 N and not more than 0.5 N in the pretreatment step.

3. The method according to claim 1, wherein the pretreatment liquid contains an anionic surfactant.

4. The method according to claim 3, wherein the pretreatment step is carried out under heat.

5. The method according to claim 1, wherein the immunoassay is a sandwich immunoassay.

6. The method according to claim 5, wherein the sandwich immunoassay is a sandwich ELISA.

7. The method according to claim 5, wherein the pretreatment liquid contains an acidifier.

8. The method according to claim 6, wherein the biological sample comprises serum.

9. A method of measuring, by immunoassay, thyroglobulin in a sample separated from a body, the method comprising (a) a pretreatment step of mixing the sample separated from a body with a pretreatment liquid to produce a pretreated sample, said pretreatment liquid containing an acidifier and a cationic surfactant, and (b) subsequently mixing said pretreated sample with a buffer containing a water-soluble polymer.

10. The method according to claim 9, wherein the acidifier has a final concentration of more than 0.05 N and not more than 0.5 N in the pretreatment step.

11. The method according to claim 9, wherein the immunoassay is a sandwich immunoassay.

12. The method according to claim 11, wherein the sandwich immunoassay is a sandwich ELISA.

13. The method according to claim 12, wherein the biological sample comprises serum.

14. The method according to claim 10, wherein the cationic surfactant has a single-chain alkyl group having 10 or more carbon atoms, and a tertiary amine or a quaternary ammonium salt.

15. The method according to claim 10, wherein the cationic surfactant is a member selected from the group consisting of decyltrimethylammonium chloride, dodecyltrimethylammonium chloride, tetradecyltrimethylammonium chloride, hexadecyltrimethylammonium chloride (C16TAC), decyltrimethylammonium bromide, dodecyltrimethylammonium bromide, tetradecyltrimethylammonium bromide, hexadecyltrimethylammonium bromide (CTAB), laurylpyridinium chloride, tetradecylpyridinium chloride and cetylpyridinium chloride.

16. The method according to claim 10, wherein the amount of the cationic surfactant, in terms of the concentration after mixing with the sample, is 0.1% to 15%.

17. The method according to claim 9, wherein the cationic surfactant is the only surfactant.

* * * * *